United States Patent [19]

Gouet et al.

[11] 4,443,547

[45] Apr. 17, 1984

[54] ANIMAL VACCINE AGAINST COLIBACILLOSIS, PREPARATION AND USE

[75] Inventors: Philippe Gouet, Beaumont; Michel G. Contrepois; Henri-Charles Dubourguier, both of Clermont-Ferrand; Jean-Pierre Girardeau, Romagnat; Hubert L. J. Goby; Thérèse M. Goby, both of Nevers; Anne M. Goby, Varennes Vauzelles; Geneviève Goby, La Chapelle St Ursin, all of France

[73] Assignee: Institut National de la Recherche Agronomique, Paris, France

[21] Appl. No.: 375,541

[22] Filed: May 6, 1982

Related U.S. Application Data

[62] Division of Ser. No. 193,449, Oct. 3, 1980, Pat. No. 4,343,792.

[30] Foreign Application Priority Data

Oct. 3, 1979 [FR] France ............................. 79 24665

[51] Int. Cl.$^3$ ...................... C12N 1/20; C12N 15/00; A61K 39/108
[52] U.S. Cl. ..................................... 435/253; 424/92
[58] Field of Search ........................... 424/92, 88, 101; 435/253, 172

[56] References Cited

U.S. PATENT DOCUMENTS 3,975,517  8/1976  Wilson .................................. 424/92
4,237,115 12/1980  Briton, Jr. ............................ 424/92
4,298,597 11/1981  Acres et al. .......................... 424/92
4,338,298  7/1982  Myers ................................... 424/92

OTHER PUBLICATIONS

Acres et al., *Infection and Immunity*, vol. 25, pp. 121–125, 1979.

Nagy, B., *Infection and Immunity*, vol. 27, pp. 21–24, 1980.

Myers, L., *Proceeding 2nd International Symposium on Neonatal Diarrhea*, Oct. 3–5, 1978, U. of Saskatchewa, pp. 427–437.

*Primary Examiner*—Blondel Hazel
*Attorney, Agent, or Firm*—Oblon, Fisher, Spivak, McClelland & Maier

[57] ABSTRACT

It contains antigens coming from original strains of *E.coli* (Y+, 31A+ and 47A+) and the known K99 antigen.

Application to the vaccination of cows before giving birth for the protection of newborn calves against diarrhea.

3 Claims, 3 Drawing Figures

ANIMAL VACCINE AGAINST COLIBACILLOSIS, PREPARATION AND USE

This is a division of application Ser. No. 193,449, filed Oct. 3, 1980 now U.S. Pat. No. 4,343,792.

The present invention relates to the field of animal vaccines. It relates more particularly to a vaccine permitting anti-colibacillary prophylaxis of diarrhea in newborn animals, such as calves. The invention also has as an object a process for obtaining such a vaccine, vaccine preparations prepared for administration and applications of said preparations.

Since 1960 and especially since 1970 considerable work has been carried out to study the influence of enteropathogenic *E. coli* in diarrhea of newborn animals, and vaccine corresponding to various types of antigens isolated in these bacteria has already been proposed or marketed. The bibliographic reference illustrating the prior art are numerous. One skilled in the art may, for example, consult the article by S. D. Acres et al "Immunization of Calves Against Enterotoxigenic Colibacillosis by Vaccinating Dams with Purified K99 Antigen and Whole Cell Bacterins" in "Infection and Immunity," July 1979, page 121–126, Vol. 25, No. 1. This article cites a considerable number of pertinent prior art publications which are also incorporated by reference in the present specification. Supplementarily and without the following list being of an exhaustive nature, the following references may also be cited:

J. M. Rutter (1975)
Escherichia coli infection in piglets: Pathogenesis, virulence and vaccination
The Vet. Record, Feb. 22, 1975
M. R. Wilson (1974)
Immunity to *E. coli* in pigs; efficiency of a live formalized vaccine under field conditions
Brit. Vet. J. 130, page 599
J. L. Nagy, P. D. Walker, B. S. Bhogal, T. MacKenzie
Evaluation of *E. coli* vaccines against experimental enteric colibacillosis
Wellcome, Europe Information, No 6, Autumn 1978
Un vaccin qui empêche l'adhésion des bactéries (A vaccine for preventing bacterial adhesion)
I. Ørskov, F. Ørskov, H. W. Smith, W. J. Sojka (1975)
The establishment of K99, a thermolabile transmissible *E. coli* K antigen, previously called "Kco" possessed by calf and lambs enteropathogenic strains Acta.Part. Microbiol. Scand. Sect. B 83 31–36 (1975)
P. A. M. Guinee, J. Veldkamp, W. H. Jansen (1977)
Improved Minca medium for the detection of K99 antigen in calf enterotoxigenic strains of *E. coli*
Inf. & Immunity 15, 2, 676–678
J. A. Morris, A. E. Stevens, W. J. Sojka (1977)
Preliminary characterization of cell free K 99
antigen isolated from *E. coli* B 41 J. of Gen. Microbiol. 99, 353–357 L. L. Myers (1976)
Vaccination of cows with an *E. coli* bacterin for the prevention of naturally occuring diarrheal disease in their calves Am. J. of Vet. Res. 37, 7, 831–834
W. J. Sojka, C. Wray, J. A. Morris (1978)
Passive protection of lambs against experimental enteric colibacillosis by colostral transfer of antibodies from K99 vaccinated ewes,
J. Med. Microbiol. 11, 493–499
J. W. Costerton, G. C. Geesey, K. J. Cheng (1978)
Comment collent les bactéries (How bacteria adhere)
Pour la Science No 5.

In particular, the last article mentioned, taken from the review "Pour la Science," No 5, 1978 illustrates the attachment properties of bacteria to the epithelia.

A brief summary of the knowledge acquired in the prior art in the filed of anti-colibacillary vaccinations will now be presented. The bacterium carries flagelli having H antigen. It may also have particular proteic antigens, for example, of the K88 or K99 type. The capsular envelope carries the K antigens. As for the bacterial wall it carries somatic or O antigens. The work by Orskov at the International Enterobacterial Center of Denmark, has revealed a particular K88 antigen the synthesis of which is encoded by a plasmid. This antigen confers upon *E. coli* properties for attachment to the intestinal epithelium of piglets. Following this work there has been proposed and marketed vaccines for use on sows containing K88 antigen. These vaccines stimulate protection given by the colostral antibodies. In the same way other structures of *E. coli* called 987 P responsible for the attachment of *E. coli* to the intestinal epithelium of piglets have been revealed.

A K antigen (Kco) common to the enteropathogenic strains of *E. coli* of bovine or ovine origin has also been revealed. This antigen has been characterized and included in the international nomenclature under the designation K99. Its synthesis is also encoded by a plasmid. (See in particular, the publication by I. Ørskov et al "The establishment of K99, a thermolabile, transmissible *E. coli* K antigen, previously called "Kco" possessed by calf and lambs enteropathogenic strains", Acta. Path. Microbiol. Scand. Sect. B 83 31–36 1975) Culture media specially suited for seeking *E. coli* K99+ was then proposed. The biochemical characterization of K99 was also achieved. It follows from the above-cited publications as well as others that K99 antigen is now adequately defined and accessible to those skilled in the art.

In the realm of practical applications, in particular with a view to anti-colibacillary prophylaxis in cattle, numerous vaccines corresponding to the different O serological types (wall antigen) and sometimes the membrane (K antigen) have been proposed and marketed. For example, a vaccination with the B44 strain of *E. coli* has been carried out which was shown to contain the K99 antigen. The results of such a vaccination are satisfactory for some herds but do not permit complete prophylaxis of the animals treated. The principal research involved protecting calves, but K99 antigen-based vaccines have also been used for colostral protection of lambs by vaccination of ewes.

Generally speaking, use has been made to date of K88, K99, 987 P antigens and practically all the "pili" of *E. coli*. It is now recognized that the epithelia attachment factor plays a very important role in the development of prophylaxies. Until now, however, it has been difficult to demonstrate experimentally the attachment properties of *E. coli*. In the scope of his work relating to the purification and structure of attachment K88 and K99 antigens, J. P. Girardeau has developed an in vitro model on easily prepared, isolated intestinal villosities which, after contact with a suspension of *E. coli*, permit the viewing of the attachment or nonattachment on the villosity under a microscope.

This in vitro model has made it possible to show that the bacteria possessing the K99 antigen becomes attached but other K99-bacteria also have this property. The Girardeau technique, which has not yet been published, consists in using the villosities isolated from animal intestines (rabbits or calves) kept by freezing or in a formal buffer. These villosities, placed in contact with the bacteria being studied for 15 minutes, then are observed with phase contrast optical microscopy. The hairy edge of the villosity and the bacteria attached thereto may be easily distinguished. The degree of attachment is evaluated by counting bacteria fixed to the edge of the villosity.

The present invention, taking advantage of the technique proposed by Girardeau for demonstrating new systems of *E. coli* attachment, first of all made it possible to isolate and characterize the filed strains of *E. coli* in calves affected by diarrhea. Said strains are designated Y+, 31A+ and 47A+. Standard strains are respectively entered in the Collection Nationale de Cultures de Microorganisms (CNCM) maintained at the Institut Pasteur, 28 rue du Docteur Roux, Paris 15th, where they have been given respective catalog registration numbers I-104, I-105 and I-106.

The new strains employed according to the invention have been characterized as it will be shown hereinbelow, by their ability to furnish specific antigens. The other characteristics of the strains, known to the applicants, are indicated in the tables hereinbelow.

TABLE I

| Strain | Antigens K99 | Y | 31A | 47A | Enterotoxin TSa* | Characterization API** | Antibiogram*** A | S | K | C | T | Su | Tnp | Gen |
|---|---|---|---|---|---|---|---|---|---|---|---|---|---|---|
| 11A (Y+) | + | + | − | − | + | 5144552.1 | − | + | + | + | + | + | − | − |
| 31A | − | − | + | − | − | 5144572.1 | − | + | + | + | + | + | − | − |
| 47A | − | − | − | + | − | 5144552.1 | + | + | − | − | + | + | − | − |

*Thermostable enterotoxin a
**API characterization established over 24 characters

***Antibiogram { − = sensitive / + = resistant }

A = ampicillin
S = streptomycin
K = kanamycin
C = chloramphenicol
T = tetracycline
Su = sulfamide
Tnp = trimethoprime
Gen = gentamycin

TABLE II

| Biological characteristics of the standard strains | | | |
|---|---|---|---|
| | 11A | 31A | 47A |
| Glycerol | + | + | + |
| Erythritol | − | − | − |
| D-arab | ± | + | + |
| L-arab | + | + | + |
| Ribose | + | + | + |
| D-xylose | + | + | + |
| L-xylose | − | − | − |
| Adonitol | + | − | − |
| Methyl-xyloside | − | − | − |
| Galactose | + | + | + |
| D-glucose | + | + | + |
| Levulose | + | + | + |
| D-mannose | + | + | + |
| L-sorbose | − | + | + |
| Rhamnose | + | + | + |
| Dulcitol | − | + | + |
| Meso-inositol | − | + | − |
| Mannitol | + | + | + |
| Sorbitol | + | + | + |
| Methyl-D mannoside | − | − | − |
| Methyl-D glucoside | − | − | − |
| N—acetyl-glucosamide | + | + | + |
| Anygdalin | − | − | − |
| Arbutin | ± | − | − |
| Esculin | + | − | − |
| Salycon | + | − | − |
| D-cellobiose | − | − | − |

TABLE II-continued

| Biological characteristics of the standard strains | | | |
|---|---|---|---|
| | 11A | 31A | 47A |
| Maltose | + | + | + |
| Lactose | + | + | + |
| D-melibiose | + | + | + |
| Saccharose | − | + | + |
| D-trehalose | + | + | + |
| Inulin | − | − | − |
| D-melezitose | − | − | − |
| D-raffinose | − | + | + |
| Dextrin | ± | − | − |
| Amylose | − | − | − |
| Starch | − | − | − |
| Glycogen | − | − | − |

TABLE III

| Biological characteristics of the field strains (populations) | | | | | | |
|---|---|---|---|---|---|---|
| | Serology negative* | K99 | K99-Y | 31A-Y | 31A | Y |
| Number of strains | 169 | 11 | 17 | 23 | 54 | 37 |
| Saccharose | 56.2 | 0 | 5.9 | 56.5 | 57.4 | 75.7 |
| Raffinose | 65.7 | 0 | 5.9 | 91.3 | 94.4 | 78.4 |
| Dulcitol | 50.9 | 0 | 5.9 | 47.8 | 88.9 | 40.5 |
| Inositol | 28.4 | 0 | 0 | 95.6 | 59.2 | 43.2 |
| Sorbitol | 68.6 | 27.3 | 5.9 | 65.2 | 64.8 | 70.3 |
| Ampicillin | 66.3 | 90.9 | 100 | 69.6 | 63 | 86.5 |
| Carbenicillin | 53.0 | 72.3 | 17.6 | 56.5 | 61.1 | 70.3 |
| Cephalexine | 20.7 | 27.3 | 82.4 | 60.9 | 1.8 | 59.4 |
| Streptomycin | 83.4 | 100 | 82.4 | 100 | 90.4 | 94.6 |
| Kanamycin | 65.1 | 72.7 | 82.4 | 91.3 | 59.3 | 89.2 |
| Chloramphenicol | 66.3 | 100 | 82.4 | 91.3 | 88.8 | 89.2 |
| Tetracycline | 75.7 | 100 | 35.3 | 100 | 96.3 | 86.5 |
| Sulfamides | 84.6 | 100 | 82.4 | 100 | 100 | 100 |
| Nalidixic | 0 | 0 | 0 | 0 | 1.8 | 0 |
| Trimethoprime | 18.9 | 0 | 0 | 60.9 | 5.5 | 43.2 |
| Colicin | 35.5 | 36.4 | 0 | 56.5 | 31.5 | 37.8 |

*Serology negative means that an attachment antigen was not identified.
The numbers in Table III indicate the percentage of strains having the characteristic considered.
Certain strains carry both K99 and Y antigens. It is thereforeimportant to dispose of a vaccine furnishing antidodies against these two antigens.
Tables II and III hereinabove respectively provide the characteristics of the standard strains and the filed strains. It goes without saying that a fieldstrain may be used according to the invention instead of the corresponding standard strain,since it has general characteristics similar to the latter.

The object of the present invention is an anti colibacillary vaccine having enhanced effectiveness with respect to prior vaccines which were incapable of immunizing treated animals against the attachment structures of *E. coli* essentially responsible for intestinal disorders in these animals.

The invention therefore relates to an anticolibacillary animal vaccine essentially characterized in that it contains at least one antigen from the strains of *E. coli* selected among the strains Y+, 31A+ and 47A+.

According to a particularly preferred embodiment of the invention the novel vaccine contains, in addition, the antigen K99.

Thus, a highly preferred vaccine according to the invention contains antigens K99 and Y in association with antigens 31A and/or 47A or not. As an alternative, the vaccine may contain K99 and 31A antigens in association with antigens Y and/or 47A, or not.

The object of the invention is also the novel strains of *E. coli* carrying antigens 31A, Y and 47A.

A strain of *E. coli* according to the invention is characterized in that it comprises the F(31A) surface antigen recognizable by seroagglutination with a specific antiserum of this antigen, prepared from the standard strain (collection No I-105 at the Institut Pasteur), said antiserum not recognizing K99 antigen (strain of reference B41), Y antigen (collection No I-104) or 47A antigen (collection No I-106).

Another *E. coli* strain according to the invention is characterized in that it comprises the F(Y) surface antigen recognizable by seroagglutination with a specific antiserum of this antigen, prepared from the standard strain (collection No I-104), said antiserum not recognizing K99 antigen (reference strain B41), 31A antigen (collection No I-105) or 47A antigen (collection No I-106).

Another strain according to the invention is characterized in that it comprises F(47A) surface antigen recognizable by scroagglutination with a specific antiserum of this antigen, prepared from the standard strain (collection No I-106), said antiserum not recognizing the K99 antigen (reference strain B41), 31A antigen (collection No I-105) or Y antigen (collection No I-104).

The surface antigens carried by the strains of *E. coli* used according to the invention may be observed under an electronic microscope. This method therefore constitutes one of the preliminary methods of recognizing the existence of such attachment structures on the *E. coli*.

A very interesting and original technique for the study of attachment in vitro consists in using the isolated villosities of young animals (rabbits or calves) kept by freezing or in a formol buffer. These villosities placed in contact for 15 min. with bacteria to be studied are then observed with phase contrast optical microscopy. The hairy edge of the villosity and the bacteria attached thereto may be easily distinguished. The degree of attachment may be evaluated by counting the bacteria fixed to the edge of the villosity. The competition between the receiver sites and the substances added in the buffer may bring about the inhibition of the attachment and thus reveal the molecules involved in the attachment. Thus it has been possible to demonstrate the inhibition of the attachment of the Y+ strains by N-acetyl-glucosamine on calf villosities.

The utilization of competitors having more affinity for the attachment site makes the localization of the receiver possible. The lectin of wheat germ, specific to N-acetyl-glucosamine, inhibits Y attachment upwards of 100 μg. This inhibition is due to the receiver site localized on the intestinal villosity and the attachment antigen recognizes this site by a stereospecific structure of proteic nature.

Y, 31A and 47A antigens have a greater affinity for calf villosities whereas antigen K99 shows less specificity between villosities of different origins. Under the electron microscope Y antigen resembles K99 antigen, although denser, with the formation of large bunches of self-agglutinous fibers. The other antigens 31A and 47A more closely resemble "pili" although they are distinctly smaller. In general, the strains having these new structures are not enterotoxinogenic (in the young mouse model) but their frequency among animals having digestive problems is considerable. By way of illustration a survey carried out on an experimental herd showed that among 20 calves affected with diarrhea, 13 were carriers of a Y+ strain of *E. coli*.

With a view to protecting newborn animals the vaccine according to the invention is given to the dam. The newborn animal is then protected when it absorbs the colostrum of its dam.

An object of the invention is also a process for obtaining the above-defined vaccine. In conformity with this process the strains of *E. coli* carrying the antigens considered are cultivated separately, the bacteria thus respectively cultivated are collected, the respective bacterial cultures are mixed, the mixture of bacteria is inactivated and the desired vaccine is obtained, optionally, after adding an additive to this mixture.

In practice, the strain of *E. coli* carrying K99 antigen may advantageously be the strain B41, known to those skilled in the art, and revealed at the International Enterobacterial Center in Copenhagen. The other strains carrying the Y, 31A and 47A antigens are original and have been defined above.

In the course of work which led to the present invention a culture medium particularly suited to the strains of *E. coli* used, in particular the strain carrying the K99 antigen, was also found. It was discovered that the synthesis of the K99 antigen is inhibited in the presence of L-alanine. A preferred culture medium is therefore an aqueous buffered agar solution medium containing, inter alia, amino acids, glucose and mineral salts, said medium being more particularly characterized in that it contains at most 0.3 g/l of alanine. The medium advantageously contains, by way of a supplement, aspartic acid.

In its preferred embodiment the culture medium has the following composition in g/liter:

| | |
|---|---|
| agar medium | 10 to 20 g of agar |
| medium buffered to pH 7.5 | (phosphates) |
| amino acides (peptone) | 1 to 5 g |
| glucose | 1 to 5 g |
| aspartic acid | 0 to 4 g |
| Na deoxicholate | 0 to 2 g |
| yeast extracts | 0 to 1 g |
| mineral salts ($MgCO_4$, $MnCl_2$, $FeCl_2$, $CaCl_2$) | from 0.01 to 0.0001 g |

If desired, the culture medium may be autoclaved at 120° C. The *E. coli* bacteria are cultured on the surface of the agar with or without an aqueous film (1 mm thick).

After incubation at a temperature in the vicinity of 37° C., the bacteria are collected from the surface of the agar and brought to a concentration, for example, of $10^9$ to $10^{10}$/ml.

The cultures are separately prepared for each strain containing the antigen used in the vaccine according to the invention, in the manner described above. After collection of the respective bacteria, these are mixed to furnish the vaccinal preparation containing the combination of antigens provided according to the invention.

The following stage of the process consists in inactivating the *E. coli* bacteria. For this purpose, the means of inactivation known in the field of vaccines are used, i.e., chemical means or physical means. As regards chemical means, formaldehyde is advantageously used. Preferably, the commercial solution (30% formaldehyde) is used, in a proportion of 0.5% of said solution with respect to the total volume of the medium to be treated, in which case the duration of inactivation at 37° C. is about 24 hours. The physical means may consist in irradiation by gamma rays. The radiation dose will depend on the bacterial concentration in the preparation. When this is of the order of $10^9$ to $10^{10}$/ml, the dose of gamma radiation may be of the order of 0.1 to 1 Mrad. The irradiation with gamma rays has given the best results.

It is often advantageous to add to the vaccinal preparation containing the inactivated bacteria an additive of the type known in this art, for example, aluminum hydroxyde. One may add, for example, colloidal aluminum hydroxide in a proportion of 1 to 3 mg/ml with respect to the final liquid preparation. Supplementarily saponin may also be added, in which case the concentration of saponin will be from 0.5 to 3 mg for 2 to 5 ml of the total preparation.

In the final vaccinal preparation, the proportions of the inactivated bacteria carrying the respective K99,Y,31A and 47A antigens are not critical. Moreover, certain *E. coli* bacteria carrying the K99 antigen may also carry the Y antigen. As a general rule, however, it is preferred that the various antigens be present in substantially equal proportions in the vaccinal preparation.

The vaccinal preparation of the invention is employed as a subcutaneous injection.

The invention also relates to the application of the vaccine and the vaccinal preparation defined above with a view to anti/colibacillary prophylaxis of diarrhea in newborn animals, in particular the newborn calf. Although the most interesting results have been obtained with calves, the invention is equally applicable for the treatment of piglets and lambs. With a view to its application, the vaccinal preparation is injected, notably subcutaneously, to pregnant dams in the period running between 15 and 90 days, preferably between 20 and 40 days, before giving birth, in the case of prophylaxis of calves. In the field, 2 to 5 ml of vaccinal preparation containing $5 \times 10^9$ to $5 \times 10^{10}$ bacteria in total are injected into pregnant dams.

The results of vaccination tests carried out in the field demonstrate the protective effect of the colostrum of vaccinated cows on the newborn calves. It has been found that the vaccinal preparation was well tolerated by dams and permits high antibody contents in the colostrum to be obtained. No anaphylactic shocks were observed in the immunized cows.

The invention will now be illustrated, without in any way be limited, by the following examples. The examples 1 to 4 relate respectively to the obtention of vaccine types A,B,C and D which have been used for anti/colibacillary vaccination test in the herd of suckling cows, the calves being infected at birth under the conditions set out in example 5.

EXAMPLE 1

Obtention of vaccinal preparation A

The example relates to the obtention of a vaccinal preparation containing *E. coli* bacteria inactivated by irradiation and alumina as an additive.

The (known) strain B41 carrying the K99 antigen and two of the original strains according to the invention, respectively carrying the Y and 31A antigens. To begin with, a separate culture was made of the three strains to produce the bacterial cells. In each case the culture medium used had the following composition (on a one liter basis).

| agar medium | 20 g of agar |
|---|---|
| medium buffered to pH 7.5 | (phosphates) |
| amino acids (peptone) | 1 g |
| glucose | 1 g |
| aspartic acid | 0 to 2 g |
| yeast extracts | 1 g |
| mineral salts (MgCO$_4$, MnCl$_2$, FeCl$_2$, CaCl$_2$) | 0.01 to 0.0001 g |

The cultivations are separately made on the surface of the agar without an aqueous film. After incubation at 37° C., the bacteria of the respective cultures are collected from the surface of the agar and brought to a concentration of $5 \times 10^9$ for each of the strains.

The bacteria collected are then mixed and inactivated by gamma irradiation with the dose of 0.6 Mrad. The bacterial concentration was $5 \times 10^9$/ml.

Finally, 2 mg/ml of colloidal alumina is added to the final solution.

The vaccine A is thus obtained.

EXAMPLE 2

Obtention of vaccinal preparation B

One proceeds as in foregoing example 1, except that in order to obtain the final vaccine, supplementarily saponin is added as an additive in the preparation of 2 mg with respect to the final solution adjusted to a volume of 5 ml. The vaccine B is thus obtained.

EXAMPLE 3

Obtention of vaccinal preparation C

One proceeds as in the foregoing example 1, but instead of inactivating the bacteria by gamma irradiation the collected bacterial mixture is treated with 0.5% formol for 24 hours at 37° C. After inactivation of the bacteria, colloidal alumina is introduced as an additive in a proportion of 2 mg/ml of the final solution.

EXAMPLE 4

Obtention of vaccinal preparation D

One proceeds as in example 3 above except that there is added supplementarily to the preparation containing alumina, saponin as an additive in the proportion of 2 mg with respect to the final solution (total volume: 5 ml).

EXAMPLE 5

Immunization of the gestating cows

Vaccines A, B, C and D prepared respectively in examples 1 to 4 hereinabove have been used for field tests. By way of a control a preparation only containing a mixture of alumina and saponin was used. With a view to vaccination 5 ml of each of the previously defined preparations was injected subcutaneously into the gestating dams. The period selected before giving birth was between 15 and 90 days.

RESULTS (a) Innocuousness

Whatever type of preparation the cows showed no abnormal symptoms. A slight and passing loss of appetite appeared several hours after the injection in some of them.

In batches A and B, no anomaly during gestation or birth was observed.

In batch D, one of the calves had an intestinal occlusion at birth.

In batch C, one cow did not have any milk (cesarean), one calf was stillborn and one calf was born anorexic.

In the "control" batch, one cow aborted at about 8 months and one calf was stillborn.

(b) Immunizing capacity

Antibodies were sought in the serum and the colostrum of the control or vaccinated cows. In two control cows which gave birth belatedly anti-K99 and anti-Y antibodies were found in the serum and colostrum at birth. This may be related to a contamination by the enteropathogenic *E. coli* present in the experimental cowshed or to an earlier natural immunization. The other control cows did not have any seric or colostral antibodies.

Regardless of the type of vaccine the immunitary response of the cows was generally good after a single injection. The rates obtained were between 1/80 and 1/160 for anti-K99 and 1/160 and 1/320 for anti-Y.

Figure 1:
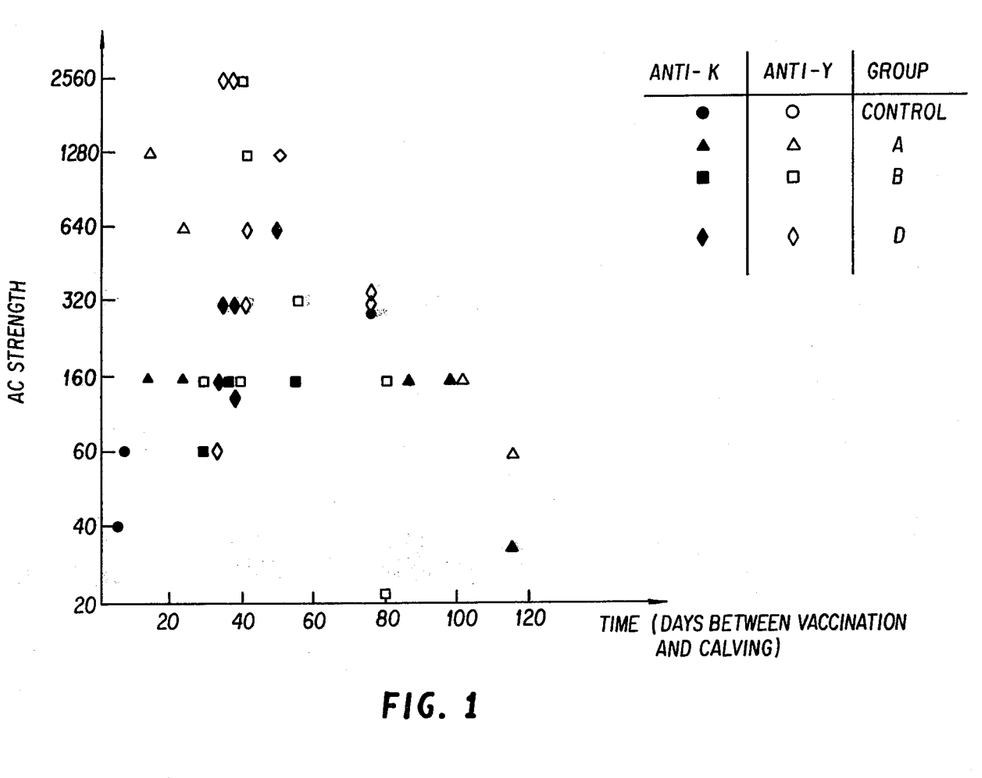

In FIG. 1 the rates obtained in the colostrum have been indicated against two antigens used as a function of the period between vaccination and giving birth. FIG. 1 is a graph with the antibody rate Ac in the colostrum marked on the ordinate and the number of days between the vaccination and giving birth on the abscissa. The colostral antibody rates are generally greater than the seric rates (concentration in the udder). The appearance of antibodies in the colostrum is very fast since 12 hours after vaccination is enough to obtain appreciable rates. The ideal vaccination period is between the 20th and the 40th day before giving birth. Beyond that period the rate diminishes notably although it remains substantial until the 80th day after vaccination.

(c) Persistence of antibodies in the milk

Figure 2:
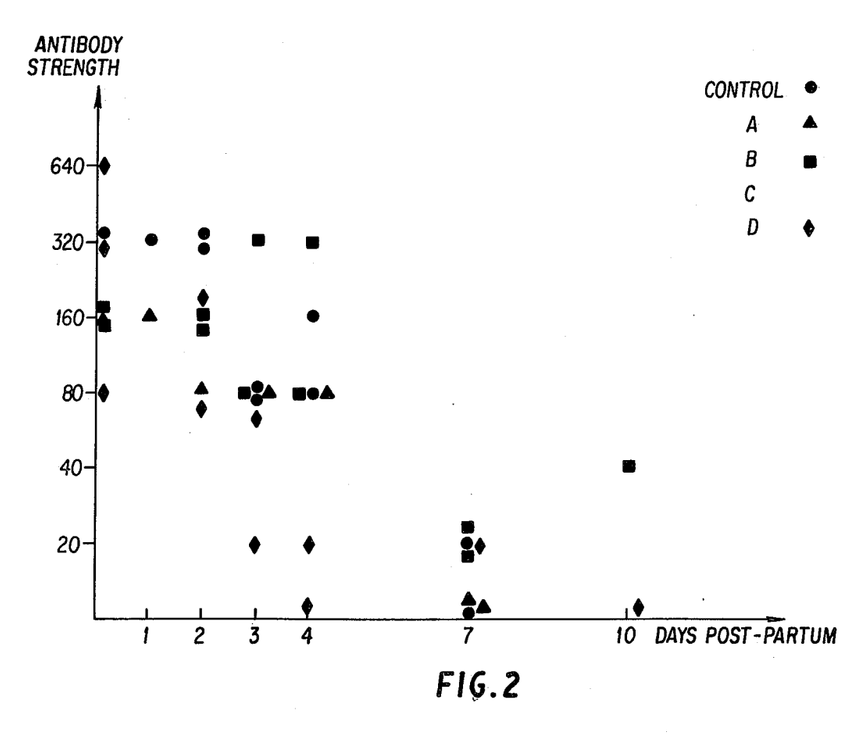

In eight cows belonging to different groups the persistence of antibodies in the udder secretions several days after giving birth was followed. The results are set out in FIG. 2 which is a graph in which the antibody rate Ac in the milk is marked on the ordinate and the number of days postpartum on the abscissa. Whatever the vaccine used or the antigen, the antibody rate is greater than 1/80 up to 2 days. Beyond this period the antibodies disappear very rapidly (1/20 at 7 days).

This result shows that if the calf is suckling properly it receives a considerable dose of antibodies at each feeding. It is protected not only by the absorption of the antibodies thereof into the blood (protection against septicaemia) but also by continuous supply of antibodies at the very site of the potential infection (digestive tract) during the period of the first four days of life. Now these four days are critical for more than 60% of morbidity (diarrhea) is attributable to enteropathogenic *E. coli*.

(d) Effectiveness of the vaccines

In table II have been compiled the results obtained after experimental infection of calves issued from vaccinated and control cows.

Figure 3:
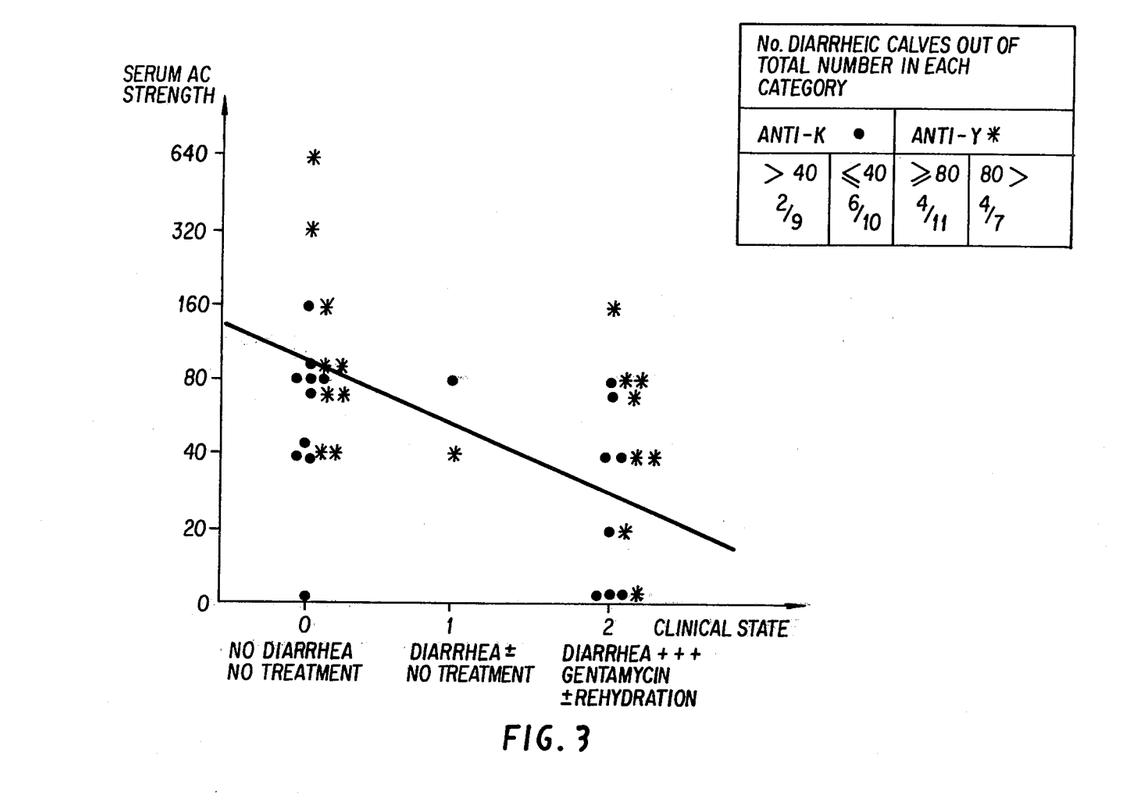

These results indicate that preparations A and D are very effective (corrected $X^2$ test, high significance). On the other hand, preparation B is ineffective despite the good colostral antibody rates. If the seric antibody rate in calves at 48 hours (FIG. 3) in this batch is examined, it is found that in three calves having diarrhea the anti-K99 rate was nil and in the fourth equal to 1/40. FIG. 3 is a graph illustrating the clinical condition of the calves and their development as a function of the seric antibody rate. The captions supplement the figure.

For all the calves their development is moreover dependent upon the seric antibody rate (FIG. 3) If their anti-K99 rate is greater than ¼ they have little chance of being sick. On the other hand for Y antigen the antibody rates are less related which is normal since the infecting strain is only K99+.

TABLE IV

| Effectiveness of the vaccines tested | |
|---|---|
| | Number of diarrhealcalves |
| Controls | 4/4 |
| Batch A | 0/5(x) |
| Batch B | 4/5(xx) |
| Batch C | |
| Batch D | ¼(x) |

(x)Corrected $X^2$test highly significant
(xx)Corrected $X^2$test not significant (e) Conclusion Under difficult experimental conditions the results obtained show the interest of the anti-colibacillary vaccines tested. The three vaccines A, B and D did not involve any vaccination risks. These vaccines are to be injected only once between the 20th and 40th day before giving birth, therefore in most cases when the cows are already in the cowshed.

The protection obtained by the calves is good since they are resistant to the experimental infection by a pathogenic *E. coli*, but on condition that the calf properly drinks the colostrum.

EXAMPLE 6

In the same manner as examples 1 to 4 vaccines A', B', C', D' were prepared corresponding respectively to the preceding vaccines A,B,C,D, using the strain B41 and the three strains of the invention Y,31A, and 47A. Thus vaccines were obtained containing the four respective antigens. Protection tests of the newborn calves have shown that the corresponding anti-colibacillary vaccines were effective. Vaccine A' proved to be the most interesting.

EXAMPLE 7

Specimens of feces of calves affected with diarrhea were collected in the Charolais region during the winter of 1977–78. After direct spreading of the fecal matter on a Minca medium [P. A. M. Guinee, J. Veldkamp, W. M. Jansen, Improved Minca medium for the detection of K99 antigen calf enterotoxigenic strains of *Escherichia coli*. Infect. Immun. 15(2): 676–678(1977)] with the addition of Polyvitex (Bio-Mérieux, Marcy l'Etoile, France, mixture of glucose and growth factors) five strains per specimen were pricked out of the agar Minca medium then examined.

The attachment of colibacilli to the intestinal villosities was studied according to the Girardeau in vitro method [J. P. Girardeau, A new in vitro technique for attachment to intestinal villi using enteropathogenic *E. coli* Ann. Microbiol. Institut Pasteur (going to press)] by direct observation under the microscope.

The K99 antigen was sought by agglutination on a slide with a specific antiserum and the production of TS toxi according to the method of the newborn mouse. [A. G. Dean, Y. Ching, R. G. Williams, L. B. Harden, Test for *Escherichia coli* enterotoxin using infant mice: application in a study of diarrhea in Honolulu, J. Inf. Dis. 125: 407–411 (1972)].

To appreciate the pathogenic potentialities of ATT+ *E. coli* of axenic calves [Ph. Gouet, Y. Riou, M. Contrepois, H. C. Dubourguier, Efficacité d'une technique simple de production d'agneaux axeniques et de veaux oligoxeniques par décontamination a la naissance (Effectiveness of a simple technique of producing axenic lambs and oligoxenic calves by decontamination at birth). Ann. Rech. Vet. 10 (1): 49–54 (1979)] not receiving colostrum were infected at birth. The clinical evolution has been observed and the moribund calves were autopsied.

To measure the protective effect of the colostral antiattachment antibody, cows have been vaccinated with a partially purified K99 antigen. The antigen associated with the Freund incomplete adjuvant was administered sub-cutaneously. The colostrum of the cows was collected then frozen. The protection conferred by the colostrum of the vaccinated cows was assessed by oral infection of newborn calves having received 2 l of the immune colostrum, compared to calves receiving a nonimmune colostrum. The following results have been obtained.

Frequency of ATT+ *E. coli*

(1) K99 antigen

Six hundred strains of *E. coli* were isolated from 120 specimens of diarrheal calf feces. Thirty percent of the strains are K99+ *E. coli*. K99+ was found in the feces of 40% of the calves aged one day to one month. This frequency reached 57% in calves of less than four days. Further, it was observed that among the 30% of the K99+ strains only 14% express their Ag K99 in the absence of glucose in the culture medium whereas for 16% the glucose was mandatory (glucose dependent strains).

(2) Other colibacilli attachment factors.

The attachment factors were sought in a sampling consisting of 47 K99+ strains and 53 K99− strains representative of all the calves.

The attachment to the villosities in vitro shows (table V) that 71% of the calibacilli strains attach themselves to intestinal villosities, 30% owing to the Ag K99 and 41% to different structures.

The study by serology and by electronic microscopy has shown that at least two other structures are responsible for the attachment of colibacilli to the intestin. One called F(Y) of 4 nm diameter, very long like Ag K99 and whose attachment to the villosities has been revealed in vitro to be distinctly stronger than K99 alone. F(Y) is present in 18% of the strains, either alone (9%) or in association with another attachment structure called F(31A)(3%):shorter and measuring 5 nm in diameter, it is present in 8% of the strains, either alone (5%) or in association with F(Y).

Demonstration of the pathogenic capacity of *E. coli* carrying the F(31A) structure in the axenic calf.

Ten newborn axenic calves deprived of colostrum were innoculated with three different strains (A,B,C) carrying the factor F(31A)(table VI) in the amount of $10^{10}$ bacteria, orally. The strains A and B induce septicaemia with or without diarrhea. They cause suffusions at vital organs (heart, spline). Perirenal oedema is practically always observed. Nervous symptoms may translate into cerebral histological lesions. In all cases there is more or less pronounced interstitial bronchial pneumonia which may go as far as emphysema. With the strain C one out of three calves died but was not subject to a postmortem examination.

Protective effects of anti-K99 vaccination

The vaccination with a K99 antigen from strain B41(O101:K99:H−) by precipitation at pH 4 of the supernatant buffer-bacteria mixture after heating and stirring 20 min at 60° C. permitted a colostrum containing antibodies against Ag K99 (table VII) to be obtained. Anti-O-antibodies also appeared. The anti-O agglutin content is multiplied by 8 in the colostrum of vaccinated cows compared to the controls and anti-K99 agglutins totally absent in the controls, attain on the average 200 in the colostrum of the vaccinated animals.

TABLE V

The frequency of bovine strains carrying different intestinal epithelium attachment structures K99, F(Y), F(31A).

| Strains in % | K99* 1 | K99* 2 | F(Y) | F(31A) | Enterotoxin ATT | Enterotoxin TS | φnm |
|---|---|---|---|---|---|---|---|
| 14 | XXXXXXX XXXXXXX | | | | + | + | 4 |
| 10 | | XXXXXXX XXXXXXX | | | + | + | 4 |
| 6 | | XXXXXXX XXXXXXX | XXXXXXX XXXXXXX | | + | + | |
| 9 | | | XXXXXXX XXXXXXX | | + | − | 4 |
| 3 | | | XXXXXXX XXXXXXX | XXXXXXX XXXXXXX | + | − | |
| 5 | | | | XXXXXXX XXXXXXX | + | | 7 |
| 24 | | | | | + | − | |
| 29 | | | | | − | − | |

*K99 1 = glucose nondependent
K99 2 = glucose dependent

TABLE VI

Bacteriological and clinical resuls of the infection by the three strains A, B, C of E. coli F(31A)

| | | Number of E. coli/g | | |
|---|---|---|---|---|
| | cephalora-chidian liquid | blood in heart | urine | dead calves |
| E..coli A | $2 \times 10^6$ | $10^8$ | $10^7$ | 4/4 |
| E. coli B | $10^6$ | $10^5$ | $10^3$ | 2/3 |
| E. coli C | NM* | NM | NM | 1/3 |

NM* = non made.

TABLE VII

| | | Antibody content in the colostrum | | | | | | | |
|---|---|---|---|---|---|---|---|---|---|
| | | 1 | 2 | 3 | 4 | 5 | 6 | 7 | |
| Control | A | 160 | 80 | 80 | 80 | 20 | 20 | 0 | m ≃ 40 |
| cows | B | 0 | 0 | 0 | 0 | 0 | 0 | 0 | m ≃ 0 |
| Vaccinated | A | 320 | 320 | 320 | 160 | | | | m ≃ 320 |
| cows | B | 320 | 320 | 160 | 80 | | | | m ≃ 200 |

In case of an oral infection by the B41 strain the calves receiving the immune colostrum are protected almost 100% (table VIII).

In case of an infection by a K99+ heterologous strain (09:K30,K99:H−) the protection is not as good since only three animals out of six were totally protected and two even died.

TABLE VIII

Protection given by an anti-K99 colostrum in calves experimentally infected by K99+, TS+ E.coli

| Infecting strain | Number of calves | Diarrhea | Dehydration | Death |
|---|---|---|---|---|
| 0101:K99:H− | controls: 4 | 4 | 3 | 2 |
| | vaccinated: 6 | 1 | 0 | 0 |
| 09:K30,K99:H− | controls: 7 | 7 | 7 | 6 |
| | vaccinated: 6 | 3 | 2 | 2 |

The F(Y) factor of a morphology close to K99 may coexist with K99 or F(31A). With the exception of strains F(Y) which are also K99+, the TS toxin could not be detected in the F(Y) strains. It was also observed in vitro that the attachment of K99+ F(Y) strains is much stronger than that of K99 strains which may aggravate the pathogenicity of this type of E. coli.

The three F(31A) strains that were used to infect axenic calves have unquestionable pathogenic potentialities since they produce septicaemia (sic) and lesions causing death of the animals in less than 48 hours. There is no analogy with invasie strains of E. coli possessing a Vir plasmid.

These results confirm that the attachment factors of enteropathogenic and septicaemic E. coli have a very great importance.

We claim:

1. A biologically pure culture of a strain of E. coli having the F(31A) surface antigen recognizable by seroagglutination with a specific antiserum of said antigen, prepared from the standard strain (collection n°I-105 at the Institute Pasteur), said antiserum not recognizing the K99 antigen (reference strain B41), or the Y antigen (collection n°I-104), or the 47A antigen (collection n°I-106), said culture when inactivated yielding a vaccine effective in treating diarrhea in newborn animals.

2. A biologically pure culture of a strain of E. coli having the F(Y) surface antigen recognizable by seroagglutination with a specific antiserum of said antigen, prepared from the standard strain (collection n°I-104) said antiserum not recognizing the K99 antigen (reference strain B41) or the 31A antigen (collection n°I-105) or the 47A antigen (collection n°I-106), said culture when inactivated yielding a vaccine effective in treating diarrhea in newborn animals.

3. A biologically pure culture of a strain of E. coli having the F(47A) surface antigen recognizable by seroagglutination with a specific antiserum of said antigen, prepared from the standard strain (collection n°I-106), said antiserum not recognizing the K99 antigen (reference strain B41), or the 31A antigen (collection n°I-105) or the Y antigen (collection n°I-104), said culture when inactivated yielding a vaccine effective in treating diarrhea in newborn animals.

* * * * *